(12) United States Patent
Yao et al.

(10) Patent No.: US 8,280,479 B2
(45) Date of Patent: Oct. 2, 2012

(54) FLEXIBLE 3D MICROPROBE STRUCTURE

(75) Inventors: Da-Jeng Yao, Hsinchu (TW); Chang-Hsiao Chen, Taipei County (TW); Shih-Chang Chuang, Hsinchu (TW); Yen-Chung Chang, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 380 days.

(21) Appl. No.: 12/637,485

(22) Filed: Dec. 14, 2009

(65) Prior Publication Data
US 2011/0144467 A1 Jun. 16, 2011

(51) Int. Cl.
*A61B 5/04* (2006.01)
*A61N 1/00* (2006.01)
(52) U.S. Cl. ........ 600/378; 600/372; 600/377; 600/544; 607/116
(58) Field of Classification Search .......... 600/372–373, 600/377–378, 393, 544–545; 607/116–118
See application file for complete search history.

(56) References Cited

U.S. PATENT DOCUMENTS

| 2003/0100823 A1* | 5/2003 | Kipke et al. ................. 600/378 |
| 2006/0173263 A1* | 8/2006 | He et al. ........................ 600/378 |
| 2010/0144216 A1* | 6/2010 | Daniel et al. .................. 439/862 |

OTHER PUBLICATIONS

Takeuchi et al., "3D flexible multichannel neural probe array," Journal of Micromechanics and Microengineering, 2004, pp. 104-107, vol. 14.

* cited by examiner

*Primary Examiner* — Linda Dvorak
*Assistant Examiner* — Brian M Antiskay
(74) *Attorney, Agent, or Firm* — Muncy, Geissler, Olds & Lowe, PLLC

(57) ABSTRACT

The present invention discloses a flexible 3D microprobe structure, which comprises at least one probe, a base and a hinge portion. The probe is connected to the base via the hinge portion. The probe forms a bend angle with respect to a normal of the base by attracting the probe through an electrostatic force to make the hinge portion bend with respect to the base, and thus to form a 3D structure having the bend angle. The probe, the base and the hinge portion are made of a flexible polymeric material to reduce the inflammation response of creatures. Further, a fixing element is used to enhance the structural strength of the flexible 3D microprobe structure.

12 Claims, 9 Drawing Sheets

FLEXIBLE 3D MICROPROBE STRUCTURE

FIELD OF THE INVENTION

The present invention relates to a flexible 3D microprobe structure, particularly to a flexible 3D microprobe structure formed by electrostatic force.

BACKGROUND OF THE INVENTION

Recently, advance in biomedical microelectronics has greatly improved in-vivo physiological research, for example, the studies of principles and methods of the neural conduction, which may favor the neurological diagnosis and treatment. The microelectrode array, or MEA for short, not only has fine puncturing ability but also can record in-vivo electrophysiological signals. Therefore, MEA plays a very important role in the field of neural science. Further, MEA also functions as an intermediary between analog physiological signal and bio signal analysis.

A conventional planar MEA cannot fully record the electrophysiological signals. Thus, a 3D MEA is used to detect neural signals. In detection, MEA punctures tissue before detecting actional potentials of neuron, which may cause the damage or infection of tissues. Further, the neural signals from neurons need complicated time-consuming signal processing and computation. Therefore, MEA needs a long-time stability and biocompatibility.

The current MEA usually has a hard-material neural interface, such as a silicon-based material used for the neural interface. If a hard material inserted into the tissues for a long time, the mechanical mismatch between the hard material and the soft tissues may cause inflammation. The heartbeat or breath causes the pulsed movement of the tissues. The pulsed movement further results in micromotion and accelerate inflammation. Inflammation will cause neuroglia to cover the electrodes and form sheath. Thus, the electrodes are insulated from the sheath and hard to record neural signals.

MEA was made by a soft material which was not only harm tissues less but also has the advantages as follow, a excellent biocompatibility, a high signal-to-noise ratio (SNR), a low material cost, and a high suitability for long-time detection.

In Journal of Micromechanics and Microengineering, vol. 14, pp. 104-107, 2004, the Takeuchi et al. proposed a self-assembled "3D Flexible Multichannel Neural Probe Array", wherein a nickel layer is coated on a planar polymeric probe array to form a nickel layer functioning as a magnetic material. Magnetic force attracts the nickel layers to assemble the planar polymeric probe into a 3D probe array, wherein the thicker nickel layers contribute their strength to the puncturing actions. However, nickel is toxicant to organisms. Further, magnetic force is harder to control the angle of the probe. Thus, the prior art has only limited application.

SUMMARY OF THE INVENTION

The primary objective of the present invention is to provide a flexible 3D (3-dimensional) microprobe structure, which adopts a flexible material having a better biocompatibility and less likely to cause inflammation, whereby the microprobe array of the present invention can apply to creatures to record the neural signals for a long time steadily. Further, the 3D structure of the present invention can enlarge the space of performing a 3D detection on the cells of the creatures.

To achieve the above mentioned objective, the present invention proposes a flexible 3D microprobe structure, which comprises at least one probe, a base, and a hinge portion. The probe is connected to the base via the hinge portion. The probe forms a bend angle α with respect to a normal of the base by attracting the probe through an electrostatic force to make the hinge portion bend with respect to the base. The probe and the hinge portion are made of a first flexible polymeric material, and the base is made of a second flexible polymeric material so as to reduce the inflammation responses of the creatures. In one embodiment, a fixing element and an auxiliary fixing element are used to fix a bent structure formed of the probe. In another embodiment, a structure-reinforcing element is used to strengthen the probe so as to puncture a detected object by the probe, wherein the detected object may be tissues of the creatures.

Below, the technical contents of the present invention are described in detail with the embodiments and the drawings.

BRIEF DESCRIPTION OF THE DRAWINGS

The embodiments of the present invention are described in cooperation with the following drawings.

DETAILED DESCRIPTION OF THE PREFERRED EMBODIMENTS

Below, the technical contents of the present invention are described in detail in cooperation with the drawings.

Figure 1:
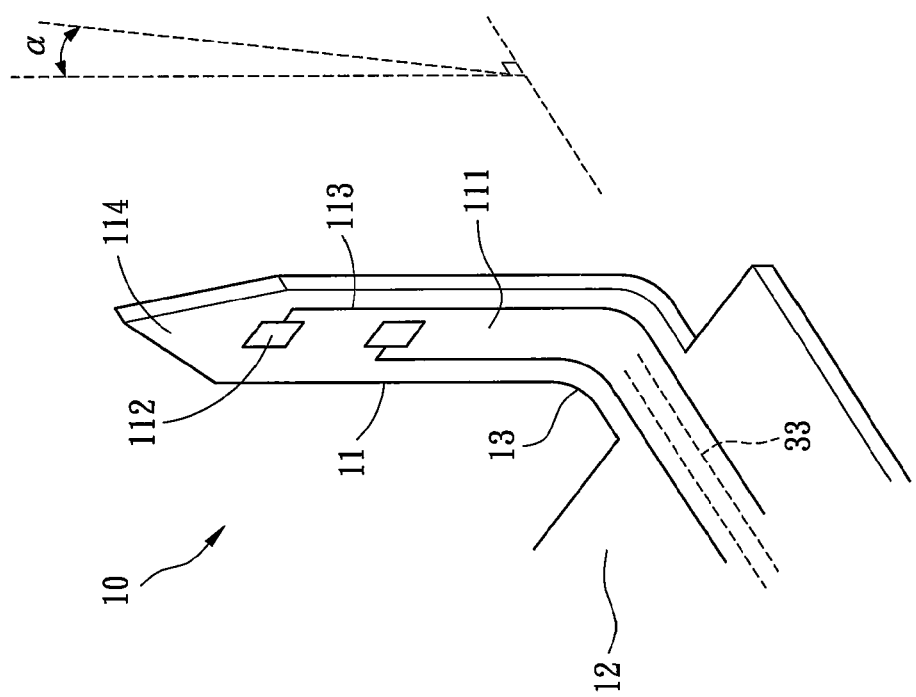
FIG. 1 is a perspective view schematically showing the appearance of a flexible 3D microprobe structure according to one embodiment of the present invention.

Refer to FIG. 1 a perspective view schematically showing the appearance of a flexible 3D microprobe structure 10 according to one embodiment of the present invention. The flexible 3D microprobe structure 10 comprises at least one probe 11, a base 12 and a hinge portion 13. The probe 11 is connected to the base 12 via the hinge portion 13. The probe 11 forms a bend angle α with respect to a normal of the base 12 by attracting the probe 11 through an electrostatic force to make the hinge portion 13 bend with respect to the base 12. The probe 11 and the hinge portion 13 are made of a first flexible polymeric material, and the base 12 is made of a second flexible polymeric material. The first and second materials are selected from a group consisting of polyimide (PI), parylene(poly-para-xylylen), a thick SU-8 photoresist, polydimethylsiloxane (PDMS), and benzocyclobutene (BCB), but the first and second materials are not limited to any one of the above mentioned materials. Thus, the flexible 3D microprobe structure 10 has a better biocompatibility and can thus obtain the biosignals in long-term recording. The present invention is exempt from the immunological rejection usually caused by toxic material or the inflammation caused by the friction of a hard material. Further, the polymeric material has a lower price and favors mass batch production.

Figure 2:
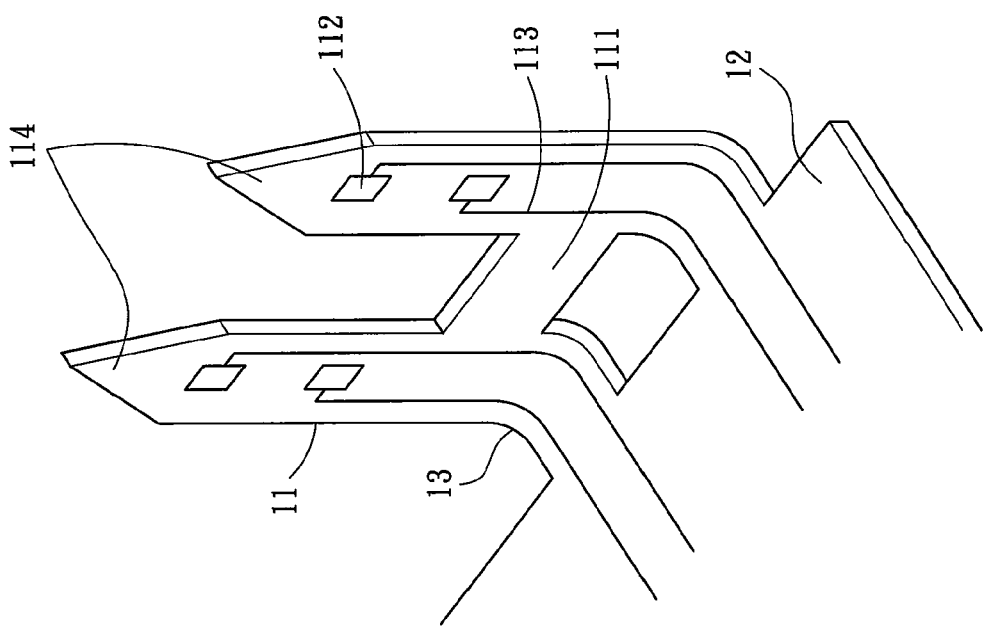
FIG. 2 is a perspective view schematically showing that a plurality of probes jointly uses a connection member according to one embodiment of the present invention.

Refer to FIG. 2 a perspective view schematically showing that a plurality of probes jointly uses a connection member according to one embodiment of the present invention. In the probe 11, the portion far away from the needle point 114 is defined to be a connection member 111. The connection member 111 is connected to the hinge portion 13. In FIG. 2, several probes 11 jointly use the same connection member 111, whereby the bend angles of the probes 11 become consistent. One or more hinge portions 13 (two hinge portions 13 in FIG. 2) are connected to the base 12 to provide the flexible 3D microprobe structure 10 with the probes 11 of plural number. Each probe 11 has at least one electrode 112, and the electrode 112 is electrically connected to the base 12 via a wire 113. It should be explained herein: the present invention does not limit the structural relationships of the probe 11, the base 12 and the hinge portion 13. In other words, the probe 11, the base 12 and the hinge portion 13 are not necessarily independent components but may be defined as different regions of the same workpiece for the convenience of describing of the relationship thereof.

Figure 3A:
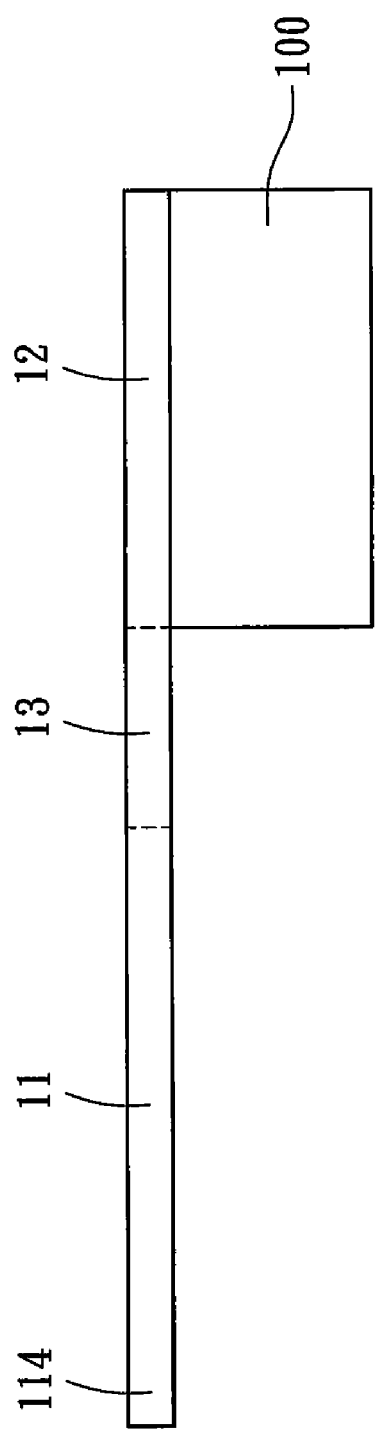
FIG. 3A is a diagram schematically showing a probe before bending according to the present invention.
Figure 3B:
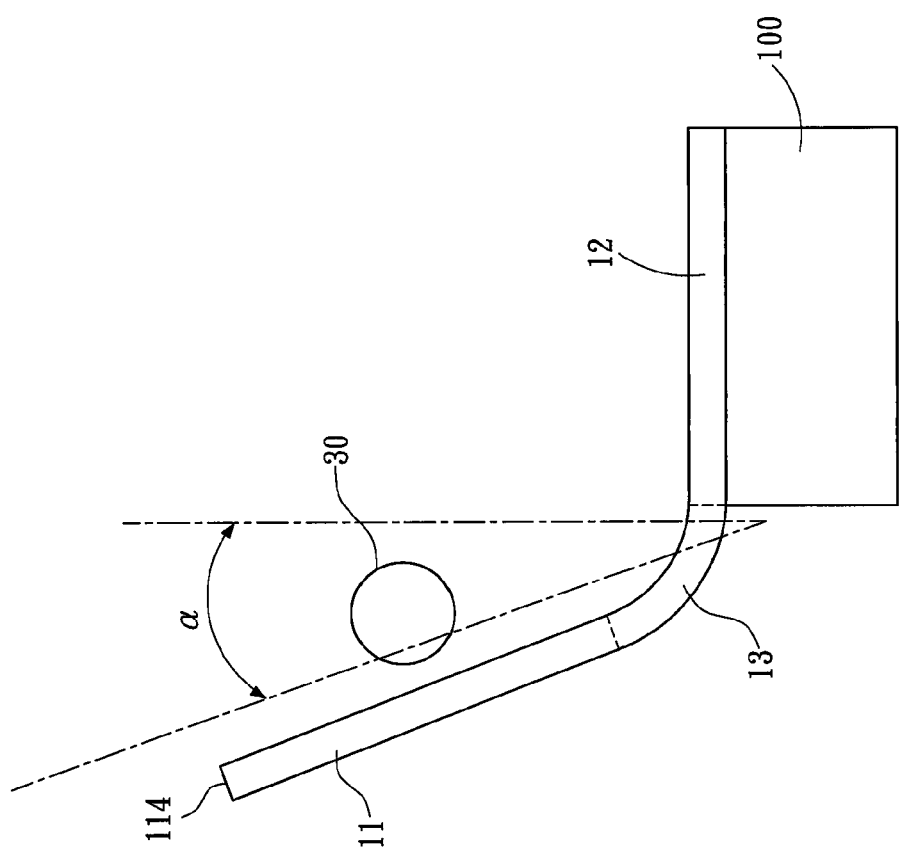
FIG. 3B is a diagram schematically showing that an electrostatic force bends the probe according to the present invention.

Refer to FIG. 3A and FIG. 3B diagrams schematically showing that an electrostatic force bends the probe 11 to form a 3D structure. As the first flexible polymeric material of the probe 11 has excellent insulator, the probe 11 can be easily induced to accumulate electric charges. In FIG. 3A, the probe 11 is unbent and fixed to a glass carrier 100. In FIG. 3B, a charged plastic rod 30 approaches the probe 11 and attracts the probe 11 to bend and have the bend angle α. The plastic rod 30 can be charged via a triboelectricity method, but electrifying the plastic rod 30 is not limited to the method. In comparison with the prior art proposed by the Takeuchi et al., the present invention neither uses a special apparatus to assemble the probe array nor deposits harmful magnetic metal on the probes. The present invention can use the electrostatic sources placed at different positions or having different electrostatic forces to attain different bend angles of the probe 11. Thus is achieved the adaptability of design and fabrication.

Figure 3C:
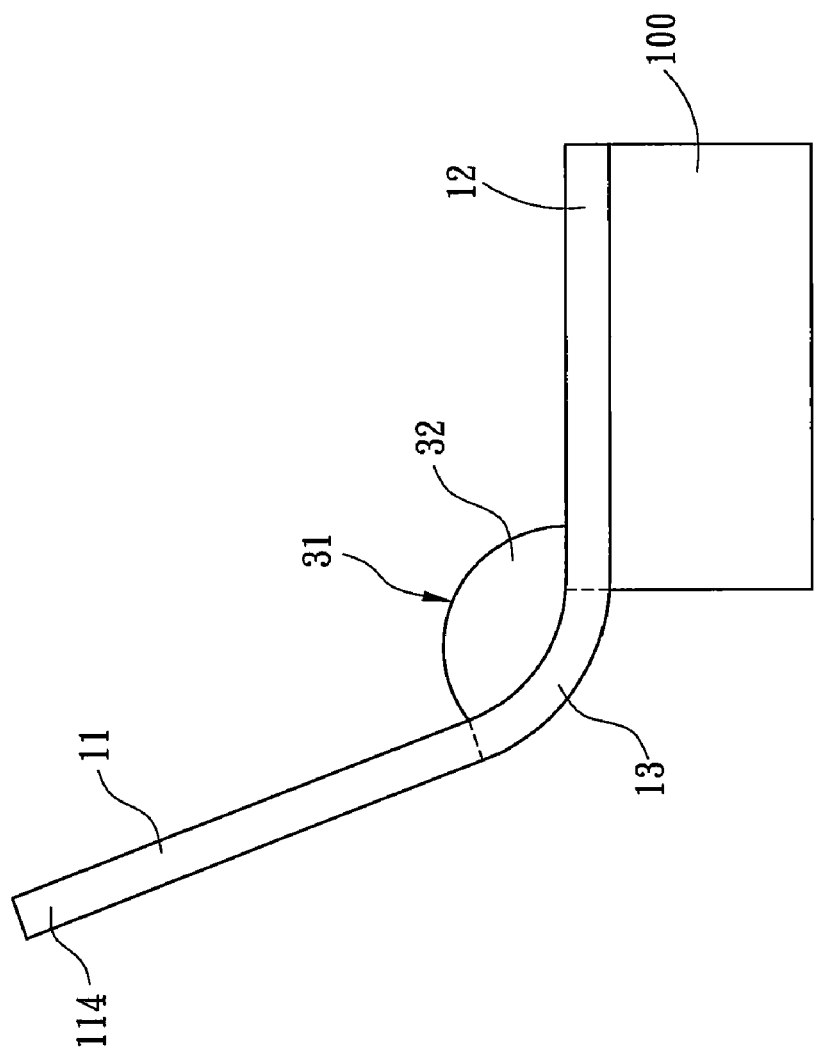
FIG. 3C is a diagram schematically showing a fixing element according to the present invention.

After the bend angle α has formed between the probe 11 and the normal of the base 12 to form a bent structure, the bent structure is fixed by the inherent plasticity of the hinge portion 13 or an additional fixing element 31. The present invention does not limit the way to realize the fixing element 31. The fixing element 31 may be in form of press-fit members respectively arranged on the base 12 and the connection member 111 or in a form of a glue 32 applied to the hinge portion 13, as shown in FIG. 3C. The glue 32 may be polyethylene glue (PEG). The PEG has a melting point of about 70° C. The high viscosity of the molten PEG is used to fix the flexible 3D microprobe structure 10. The process of bending and fixing the probe 11 is described in detail below. Firstly, the finished planar probe structure is fixed on a glass carrier 100. Next, a charged plastic rod 30 approaches the probe 11 and attracts the probe 11 through the electrostatic force. At the same time, the PEG powder is heated to become the molten PEG in the liquid state. Next, the molten PEG is applied to the hinge portion 13. Then, the molten PEG solidifies to form the fixing element 31 of the crystalline solid state and thus fix the bend angle α between the probe 11 and the normal of the base 12. The molten glue may be manually applied to the hinge portion 13 or guided by a micro channel 33 on the base 11 (shown in FIG. 1) to the hinge portion 13, to form the fixing element 31. The position where the glue 32 is applied is determined by the fixing effect of the bent structure. In FIG. 3C, the glue 32 is only applied to the hinge portion 13.

Figure 4A:
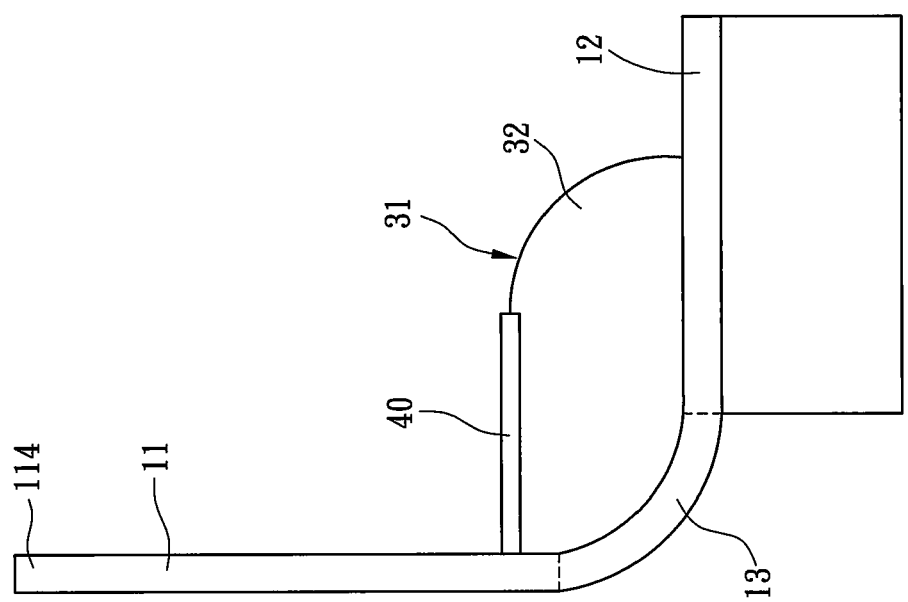
FIGS. 4A-4C are side views respectively schematically showing auxiliary fixing elements according to different embodiments of the present invention.
Figure 4B:
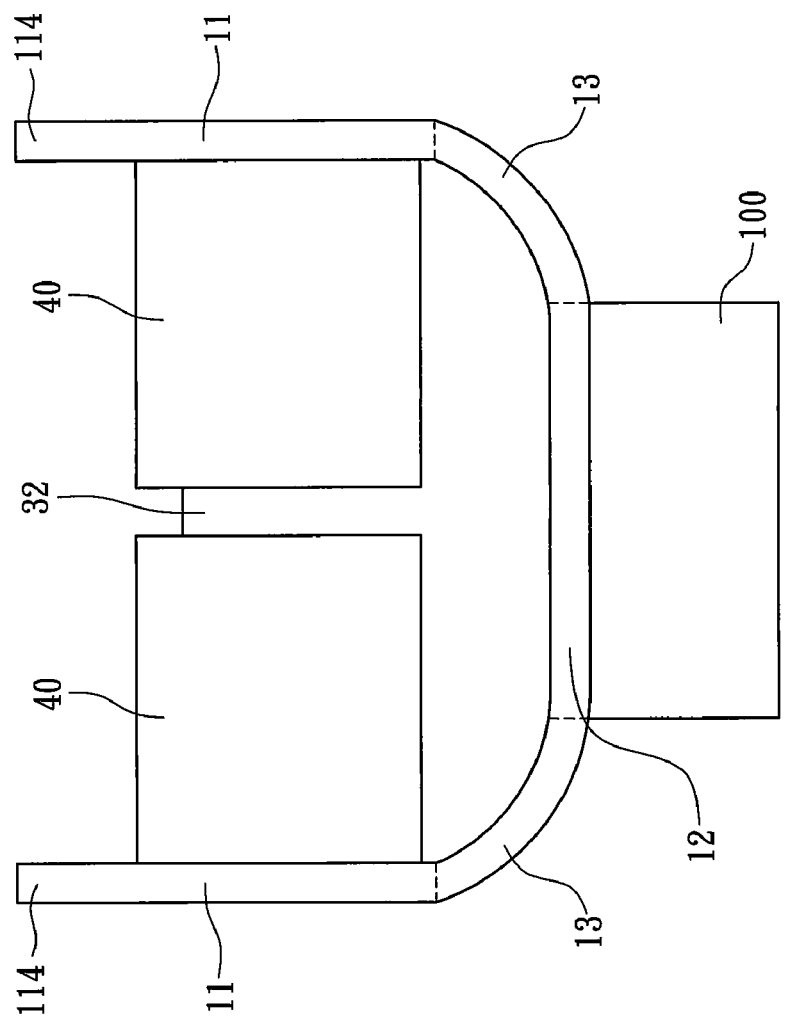
Figure 4C:
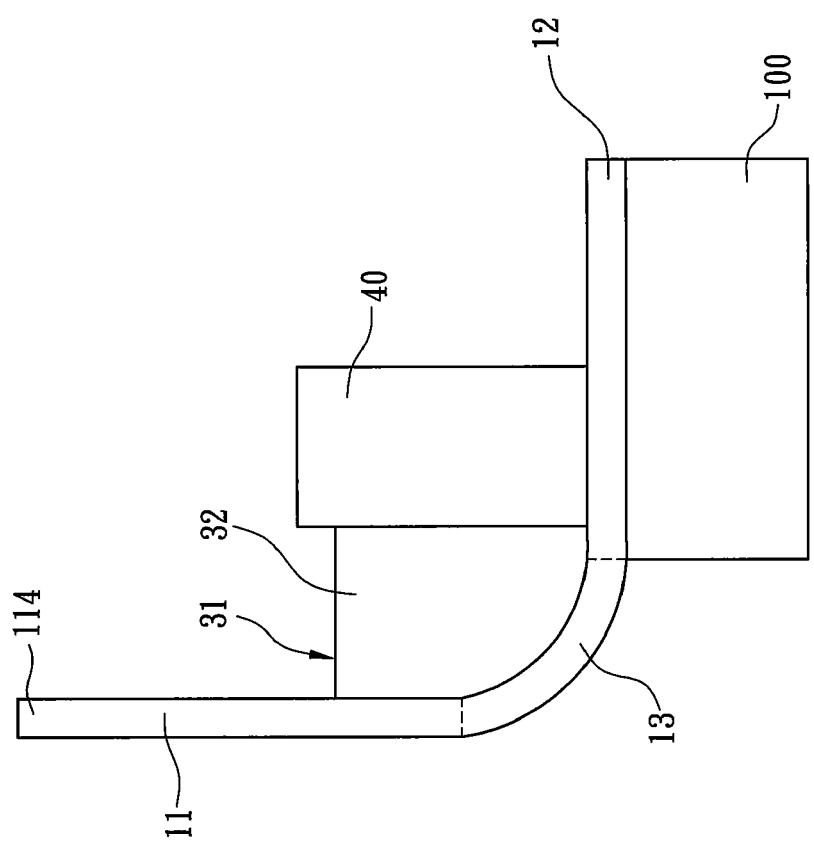

Refer to FIGS. 4A-4C. An auxiliary fixing element 40 may be added to the base 12 or the connection member 111 of the probe 11 to increase the contact area of the glue 32 and the probe 11 and enhance the fixing effect. Considering the consistency in the fabrication and the biocompatibility, the material of the auxiliary fixing element 40 is preferably selected from the high-biocompatibility flexible polymeric materials mentioned above. The present invention does not strictly limit the shape and the position of the auxiliary fixing element 40. In FIG. 4A, the auxiliary fixing element 40 is a board-like structure vertical to the connection member 111 and using the larger area thereof to assist in fixing the probe 11. In another embodiment shown in FIG. 4B, two probes 11 are arranged on two opposite sides of the base 12, and the auxiliary fixing elements 40 are block-like structures arranged on the connection members 111 of the two probes 11. When the two probes 11 are bent to each other, the auxiliary fixing elements 40 get close to form a slit, and the glue 32 can flow along the microchannel via the capillary effect to join the two auxiliary fixing elements 40. In FIG. 4C, the auxiliary fixing element 40 is a block-like structure arranged on the base 12. When the glue 32 is applied to the hinge portion 13, the auxiliary fixing element 40 functions as a wall blocking the flow of the glue 32, and the glue 32 between the probe 11 and the auxiliary fixing element 40 enhances the adhesion effect. The figures in the specification are schematic diagrams to convenience the demonstration of the present invention; they are not necessarily drawn according to the proportion.

Figure 5:
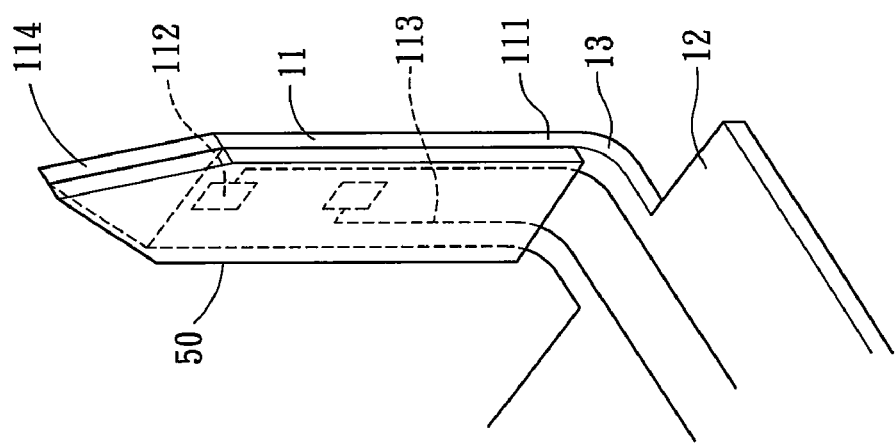
FIG. 5 is a perspective view schematically showing a structure-reinforcing element according to one embodiment of the present invention.

Considering the strengths of some flexible polymeric materials are insufficient to puncture harder tissues of the creatures, a structure-reinforcing element 50 is added to the probe 11 in one embodiment of the present invention, as shown in FIG. 5. The structure-reinforcing element 50 is made of a material having a higher strength and a better adhesion to the flexible polymeric material, such as a thick SU-8 photoresist. The structure-reinforcing element 50 is formed only on the probe 11 to form a composite-layer structure, and the hinge portion 13 maintains its original flexible material for bending. For improving adhesion, the probe 11 may be processed with oxygen plasma or a surface activation treatment before the structure-reinforcing element 50 is formed on the probe 11. The present invention does not limit the structure-reinforcing element 50 to be the composite-layer structure shown in FIG. 5. The structure-reinforcing structure 50 may be realized in various ways according to requirements. For example, the structure-reinforcing element 50 may be in form of plate-like or strip-like structures along the probe 11. Alternatively, the structure-reinforcing element 50 may only enhances the strength of the needle point 114 of the probe 11.

In conclusion, the present invention uses electrostatic force to bend the planar probe structure into a 3D structure to record more neuronal signals. The present invention uses a flexible polymeric material to fabricate the 3D microprobe structure, which has a higher biocompatibility and is less harmful to tissues of creatures. Thereby, the flexible 3D microprobe structure of the present invention can steadily record signals for a long-term. In comparison with the conventional microprobe structures were made by hard materials, the flexible 3D microprobe structure of the present invention can persistently record neural signals even when the creatures is moving. It is a breakthrough detection of in-vivo application. Further, the present invention uses the electrostatic sources placed at different positions and having different electrostatic forces to adjust the bend angles of probes having different lengths to form oblique-insertion microelectrode arrays with the bend angle α of the range between 0 and 90 degrees. In comparison with the conventional vertical-insertion microelectrodes, the oblique-insertion microelectrode array is less harmful to the cells around the microelectrodes and able to record signals of higher reliability and better quality.

The embodiments described above are only to exemplify the present invention but not to limit the scope of the present invention. Any equivalent modification or variation according to the spirit of the present invention is to be also included within the scope of the present invention.

What is claimed is:

1. A flexible 3-dimensional microprobe structure comprises at least one probe, a base, a hinge portion, and a fixing element, wherein said probe and said hinge portion are made of a first flexible polymeric material, and wherein said probe is connected to said base via said hinge portion, and wherein said probe forms a bend angle with respect to a normal of said base, and wherein said fixing element is formed by applying glue to said hinge portion.

2. The flexible 3-dimensional microprobe structure according to claim 1, wherein said first flexible polymeric material is selected from a group consisting of polyimide, parylene (poly-para-xylylen), a thick SU-8 photoresist, polydimethylsiloxane, and benzocyclobutene.

3. The flexible 3-dimensional microprobe structure according to claim 1, wherein said base is made of a second flexible polymeric material.

4. The flexible 3-dimensional microprobe structure according to claim 3, wherein said second flexible polymeric material is selected from a group consisting of polyimide, parylene (poly-para-xylylen), a thick SU-8 photoresist, polydimethylsiloxane, and benzocyclobutene.

5. The flexible 3-dimensional microprobe structure according to claim 1, wherein said probe, said base and said hinge portion are made of an identical material.

6. The flexible 3-dimensional microprobe structure according to claim 1, wherein said base has a micro channel, and said glue flows through said micro channel to apply to said hinge portion.

7. The flexible 3-dimensional microprobe structure according to claim 1, wherein said glue is polyethylene.

8. The flexible 3-dimensional microprobe structure according to claim 1, wherein said probe has a needle point and a connection member located at one side which is far away from said needle point; said connection member connects said needle point and said hinge portion.

9. The flexible 3-dimensional microprobe structure according to claim 8, wherein said connection member has an auxiliary fixing element which can increase a contact area between said glue and said flexible 3-dimensional microprobe structure.

10. The flexible 3-dimensional microprobe structure according to claim 9, wherein said auxiliary fixing element is made of a flexible polymeric material selected from a group consisting of polyimide, parylene(poly-para-xylylen), a thick SU-8 photoresist, polydimethylsiloxane), and benzocyclobutene.

11. The flexible 3-dimensional microprobe structure according to claim 1, wherein said probe has a structure-reinforcing element which is used to strengthen said probe so as to puncture a detected object by said probe.

12. The flexible 3-dimensional microprobe structure according to claim 11, wherein said structure-reinforcing element is made of a thick SU-8 photoresist.

* * * * *